(12) United States Patent
Kolomeyer et al.

(10) Patent No.: US 7,262,329 B1
(45) Date of Patent: Aug. 28, 2007

(54) PROCESS FOR MAKING INTERMEDIATES FOR FRAGRANCE COMPONENTS FROM α-CAMPHOLENIC ALDEHYDE

(75) Inventors: Gennadiy G. Kolomeyer, Jacksonville, FL (US); Jacob Oyloe, Arlington, VA (US); Douglas A. Ferone, Jacksonville, FL (US)

(73) Assignee: Millennium Specialty Chemicals, Inc., Houston, TX (US)

( * ) Notice: Subject to any disclaimer, the term of this patent is extended or adjusted under 35 U.S.C. 154(b) by 0 days.

(21) Appl. No.: 11/604,431

(22) Filed: Nov. 27, 2006

(51) Int. Cl.
*C07C 45/67* (2006.01)
*C07C 45/72* (2006.01)
*C07C 45/74* (2006.01)

(52) U.S. Cl. ...................... 568/392; 568/341

(58) Field of Classification Search ............. None
See application file for complete search history.

(56) References Cited

U.S. PATENT DOCUMENTS

| | | | |
|---|---|---|---|
| 4,052,341 A | 10/1977 | Naipawer et al. | 252/522 |
| 4,610,813 A | 9/1986 | Schulte-Elte et al. | 252/522 R |
| 4,696,766 A | 9/1987 | Naipawer | 512/8 |
| 5,840,992 A | 11/1998 | Kido et al. | 568/392 |
| 6,833,481 B2 | 12/2004 | Yamamoto et al. | 568/341 |

OTHER PUBLICATIONS

C. Cardenas and B. Kane, "Rearrangement of α-Campholenic Aldehyde," In *Proceedings of 11th ICEOFF*, New Delhi, 12-16, Nov. 1989, pp. 37-41.

*Primary Examiner*—Sikarl A. Witherspoon
(74) *Attorney, Agent, or Firm*—Jonathan L. Schuchardt

(57) ABSTRACT

A two-step aldol condensation process is disclosed. α-Campholenic aldehyde (ACA) and methyl ethyl ketone (MEK) react in the presence of a base under conditions effective to produce a mixture comprising a high yield of ketol condensation products. Dehydration of the ketols in the presence of an organic sulfonic acid provides unsaturated ketones that are valuable intermediates for fragrance components for synthetic sandalwood products. Compared with the usual one-step, base-catalyzed approach, the two-step process increases the yield of all condensation products and maximizes production of the most valuable ketone isomers.

16 Claims, No Drawings

PROCESS FOR MAKING INTERMEDIATES FOR FRAGRANCE COMPONENTS FROM α-CAMPHOLENIC ALDEHYDE

FIELD OF THE INVENTION

The invention relates to the synthesis of intermediates for fragrance components having a valuable sandalwood aroma. In particular, the invention reacts α-campholenic aldehyde and methyl ethyl ketone in a two-step aldol condensation process to improve the yield and selectivity to the most desirable ketone isomers.

BACKGROUND OF THE INVENTION

East Indian sandalwood oil has been valued for perfumery for thousands of years. The natural oil contains mostly santalol compounds that impart a soft, woody odor that is easy to adore but hard to reproduce. Unfortunately, the santalols cannot be manufactured economically. The fragrance industry has therefore identified synthetic substitutes that boast some of the odor qualities of sandalwood oil yet are more feasible to make and sell.

Several commercial products having such a sandalwood aroma derive from an aldol condensation of α-campholenic aldehyde (ACA) and methyl ethyl ketone (MEK). In general, aldol condensation reactions can be catalyzed by either acid or base. In one common method, described in U.S. Pat. No. 4,052,341, condensation and dehydration reactions proceed simultaneously in one pot using potassium hydroxide in methanol. The reaction occurs at both C1 and C3 of MEK to provide a mixture of ketones. Isomerization of α,β-unsaturated ketones to β,γ-unsaturated ketones under the reaction and distillation conditions further complicates the process. In all, five ketone products result, as shown in Scheme 1. Ketones 1, 2, 4, and 5, upon hydrogenation, provide the secondary alcohol isomers found in Sandalore™, a product of Givaudan.

Scheme 1: Aldol Condensation Products from ACA and MEK

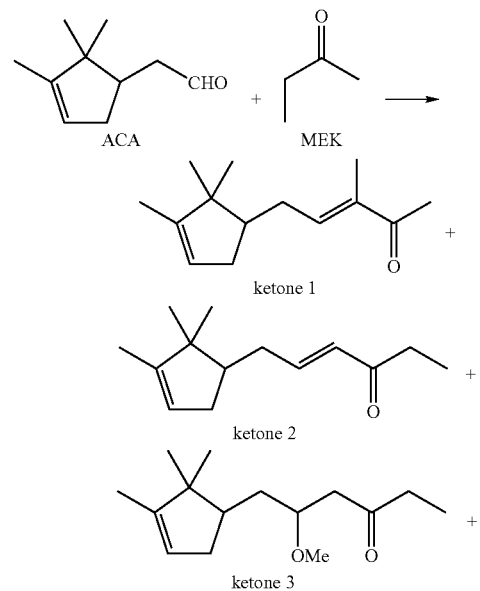

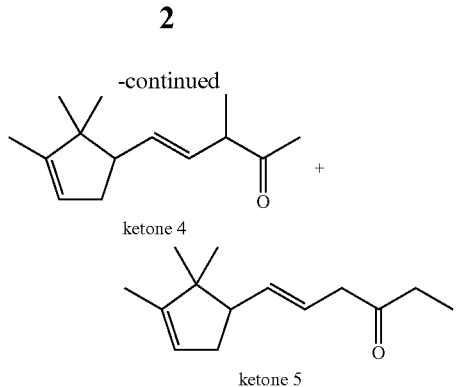

Scheme 2: Principal Components of Commercial Products

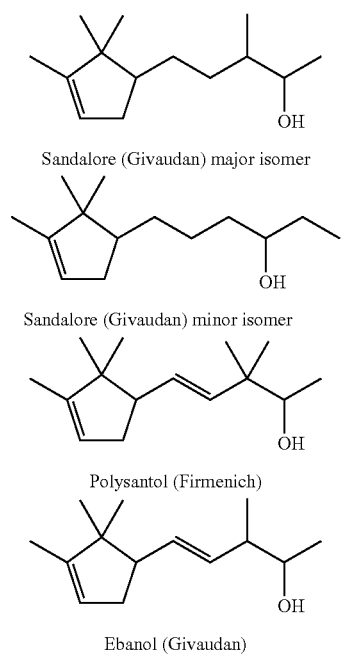

Only methyl ketones 1 and 4 can be used as precursors for making Polysantol™ (a product of Firmenich, see U.S. Pat. No. 4,610,813), and Ebanol™ (from Givaudan, see U.S. Pat. No. 4,696,766), the principal components of which are shown in Scheme 2.

While the maximum obtainable yields of the various aldol condensation products are challenging to decipher from the references noted above, we conclude that the highest yield of ketone 1 obtained from ACA is about 60%, the highest combined yield of ketones 1 and 4 is about 62%, and the best combined yield of all condensation products (ketones 1-5) is about 75%. Catalysts other than alkali metal hydroxides have been used, but the product compositions differ or the yields of the desired products are lower.

While it is generally known that aldol condensation reactions can be effected in two successive steps with different catalysts (see, e.g., U.S. Pat. Nos. 5,840,992 and 6,833,481), such a process has not been suggested for the reaction of ACA and MEK. In the typical two-step process, a base is used to produce an aldol product, and an acid (e.g., sulfuric, phosphoric, or oxalic acid) catalyzes the dehydration. The two-step process appeared to be problematic because ACA and its derivatives readily undergo acid-catalyzed rearrangements to form the corresponding β-campholenic aldehyde derivatives (see, e.g., C. Cardenas and B. Kane, "Rearrangement of α-Campholenic Aldehyde," in *Proceedings of 11th ICEOFF*, New Delhi, 12-16 Nov. 1989, pp. 37-41).

In sum, improved ways to make sandalwood aroma compounds are desirable. In particular, a better approach to aldol condensation products of ACA and MEK is needed. A valuable process would provide the highest possible yield of ketone 1, which is a common intermediate for synthetic sandalwood products, and the highest possible combined yield of methyl ketones 1 and 4, which are used to make the principal components of Ebanol and Polysantol. Ideally, the process would be easy to practice using conventional reagents and common equipment.

SUMMARY OF THE INVENTION

In one aspect, the invention is a process for making a ketol condensation product. α-Campholenic aldehyde (ACA) and methyl ethyl ketone (MEK) react in the presence of a base under conditions effective to produce a mixture comprising ketol A and ketone 1 having the structures:

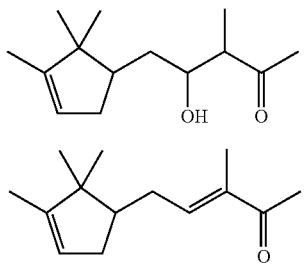

The condensation product mixture comprises at least 60 wt. % of ketol A and at least 65 wt. % of ketol A and ketone 1 combined.

In another aspect, the invention involves dehydrating this product mixture under conditions effective to produce a ketone-rich mixture comprising at least 70 wt. % of ketone 1. While most acids we tried cause undesirable rearrangement reactions, we surprisingly found that organic sulfonic acids such as p-toluenesulfonic acid uniquely catalyze the dehydration without promoting rearrangements. By exploring a two-step process of base-catalyzed condensation and sulfonic acid-catalyzed dehydration instead of the usual one-step, base-catalyzed approach, we successfully identified reaction conditions that increase the yield of all condensation products and maximize production of the most valuable ketone isomers.

DETAILED DESCRIPTION OF THE INVENTION

The invention involves the preparation of a ketol condensation product made by reacting α-campholenic aldehyde ("ACA," see Scheme 1 for structure) and methyl ethyl ketone ("MEK") in the presence of a base. The purity level of the ACA is not critical. Technical-grade material (about 85% pure) is suitable for use, but crude ACA or purified ACA could also be used. The purity level of the MEK is also not crucial. High-purity methyl ethyl ketone is readily available, but it may be more desirable to use technical-grade material or MEK recovered from the process.

Preferably, an excess of the MEK is used. Thus, the molar ratio of MEK to ACA is preferably within the range of 3:1 to 10:1, more preferably from 3:1 to 5:1. We found that an equimolar amount of MEK is often inadequate to provide an acceptable ACA conversion and at least 60 wt. % of ketol A (see Table 2).

The condensation reaction is performed in the presence of a base. The base comprises an aqueous alkali metal or alkaline earth metal hydroxide solution. Suitable bases include, for example lithium hydroxide, sodium hydroxide, potassium hydroxide, cesium hydroxide, calcium hydroxide, barium hydroxide, magnesium hydroxide, and the like, and mixtures thereof. Because it is cost-effective and easy to handle, sodium hydroxide is particularly preferred. The concentration of the base is limited to maximize production of the desired ketol product. Preferably, the base solution comprises from 0.5 to 8 wt. % of the alkali metal or alkaline earth metal hydroxide; a more preferred range is from 2 to 5 wt. %. We found that increasing the base concentration to more than 10 wt. % of the alkali metal or alkaline earth metal hydroxide can adversely impact the amount of ketol product made. Moreover, high base concentrations also generate a lower (i.e., less favorable) molar ratio of ketol A to ketol B (see Table 1).

The amount of base solution used is not particularly critical. Preferably, the base is used in an amount greater than 400 g of solution per mole of ACA, and more preferably in the range of 450 to 2500 g of base solution per mole of ACA. We found that amounts of base solution much below 400 g per mole of ACA provide relatively low ACA conversions and acceptable—although somewhat lower—yields of desirable condensation products (see Table 4).

Although the reaction of ACA and MEK can be executed within a reasonably wide temperature range, it is preferably performed at a temperature in the range of 0° C. to 50° C. A more preferred range is from 25° C. to 45° C. If the reaction temperature is too low, the reaction progresses too slowly. Temperatures greater than 50° C. are preferably avoided, however, because yields of the desired ketol can decrease significantly. For example, the 74% yield of ketol A obtained at 40° C. dips to less than 10% when the reaction temperature is increased to 80° C. (see Table 3).

The process of the invention is performed under conditions effective to produce a condensation product mixture. This mixture comprises at least 60 wt. %, more preferably at least 70 wt. %, of ketol A. In addition, the combined amount of ketol A and ketone 1 is at least 65 wt. %, more preferably at least 75 wt. %. Ketol A and ketone 1 have the structures:

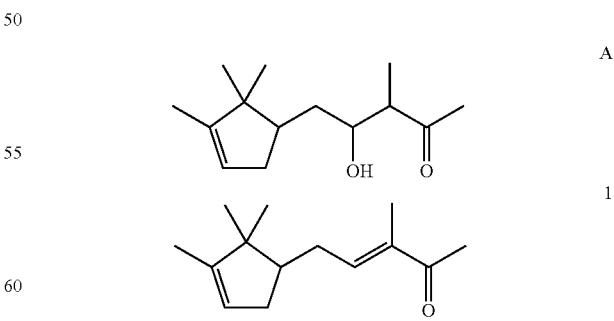

Ketol A is one or more isomers of 4-hydroxy-3-methyl-5-(2,2,3-trimethyl-3-cyclopenten-1-yl)pentan-2-one. Ketone 1 is one or more isomers of 3-methyl-5-(2,2,3-trimethyl-3-cyclopenten-1-yl)-3-penten-2-one.

The condensation product mixture usually contains additional condensation products. As shown in Scheme 1, the mixture may include one or more isomers of ketone 2, which is 6-(2,2,3-trimethyl-3-cyclopenten-1-yl)-4-hexen-3-one; ketone 4, which is 3-methyl-5-(2,2,3-trimethyl-3-cyclopenten-1-yl)-4-penten-2-one; and/or ketone 5, which is 6-(2,2,3-trimethyl-3-cyclopenten-1-yl)-5-hexen-3-one.

Commonly, the condensation product mixture also includes one or more isomers of ketol B, a precursor to ketones 2 and 5, which has the structure:

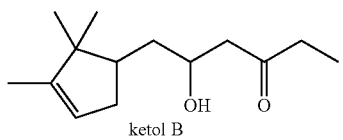

ketol B and is properly named 5-hydroxy-6-(2,2,3-trimethyl-3-cyclopenten-1-yl)hexan-3-one. The combined yield of all condensation products preferably exceeds 75 wt. %.

The condensation product mixture, which comprises at least 60 wt. % of ketol A, is a valuable intermediate for making commercially important ketones 1 and 4. Thus, the ketol-containing product mixture is preferably dehydrated under conditions effective to produce a ketone-rich mixture comprising at least 70 wt. % of ketone 1. Under the dehydration and subsequent purification conditions, some of the resulting ketone 1 can isomerize to ketone 4. Moreover, when ketol B is present, it dehydrates (and partly isomerizes) to provide ketones 2 and 5. The condensation product mixture can be distilled to isolate the ketols (see Example 1), but it is preferably used without purification in a subsequent dehydration step (see Example 17). The ketol mixture is usually just separated from the aqueous base catalyst solution and used "as is" for the dehydration.

The dehydration is performed in the presence of an organic sulfonic acid catalyst. We surprisingly found that common acid dehydration catalysts such as sulfuric, phosphoric, or oxalic acids, are unsuitable. Although these acids catalyze the dehydration, they also promote an unwanted rearrangement of the cyclopentene moiety to β-campholenic aldehyde derivatives, so the yield of ketone 1 is unacceptably low. p-Toluenesulfonic acid (p-TSA) is particularly preferred. The p-TSA can be used in any desired form; it is available commercially, for example, as the crystalline monohydrate salt or as a 65 wt. % solution in water.

When p-TSA is used as the catalyst, it is preferred to use less than 1 mole %, more preferably less than 0.5 mole %, and most preferably less than 0.3 mole %, based on the amount of ketols in the condensation product mixture.

The dehydration step can be performed over a wide temperature range. Preferably, it occurs at a temperature in the range of 25° C. to 120° C., more preferably from 35° C. to 100° C., and most preferably from 50° C. to 85° C.

The rate of dehydration and the selectivity to the desired ketones are higher when water of dehydration is removed. Preferably, the water is distilled off, along with unreacted MEK. If desired, an azeotroping agent can be included to assist in water removal. Preferred azeotroping agents are hydrocarbons such as hexanes, heptanes, petroleum ether, cyclohexane, toluene, xylenes, or the like, and mixtures thereof. The preferred method of water removal involves refluxing the reaction mixture under vacuum without addition of an azeotroping agent.

After removal of volatile materials, the distillation pot residue is preferably neutralized with a base (sodium carbonate, sodium bicarbonate, or the like), and the mixture is fractionally distilled to isolate the desired ketone condensation products (see Example 17). Uniquely, the yield of these ketones can exceed 75%. Preferably, the distilled ketone condensation products comprise more than 86 wt. % of ketone 1 or more than 86 wt. % of ketones 1 and 4 combined.

The following examples merely illustrate the invention. Those skilled in the art will recognize many variations that are within the spirit of the invention and scope of the claims.

EXAMPLES 1-3 AND COMPARATIVE EXAMPLES 4-6

Effect of Base Concentration

EXAMPLE 1

A two-liter flask equipped with a heating mantle, addition funnel, and mechanical stirrer is charged with water (576 g), 50% aqueous sodium hydroxide (24 g; provides 2% NaOH), and methyl ethyl ketone ("MEK," 264 g), and the stirred mixture is heated to 40° C. α-Campholenic aldehyde ("ACA," 85% pure, 200 g) is added dropwise, and stirring continues at 40° C. for 8 hours. The progress of the reaction is monitored using gas chromatography (GC). The analysis detects ketol A (74%), ketol B (8%), some unreacted ACA, and minor amounts of ketones 1 and 2. Selectivities (by GC): ketone 1+ketol A: 78%; all condensation products: 87%. Table 1 summarizes the results.

When the reaction is reasonably complete, the catalyst layer is removed. The organic phase is neutralized to pH=7 with acetic acid and is then washed with water. Excess MEK is removed by distillation at atmospheric pressure while keeping the pot temperature below 105° C. Vacuum distillation of the crude ketol mixture (<2 mm Hg) affords a distilled condensation product mixture (210 g, 91%) containing ketol A (84%), ketol B (9.1%), ketone 1 (5.1%), and ketone 2 (0.35%).

EXAMPLE 2

The procedure of Example 1 is repeated, except that the concentration of sodium hydroxide solution is adjusted to 0.5%. GC analysis reveals ketol A (69%), ketol B (5.6%), and minor amounts of ketones 1 and 2. GC selectivities: ketone 1+ketol A: 71%; all condensation products: 77%. See Table 1.

EXAMPLE 3

The procedure of Example 1 is repeated, except that the concentration of sodium hydroxide solution is adjusted to 5%. GC analysis reveals ketol A (63%), ketol B (11%), ketone 1 (4.9%), and ketone 2 (0.9%). GC selectivities: ketone 1+ketol A: 68%; all condensation products: 80%. See Table 1.

COMPARATIVE EXAMPLES 4-6

The procedure of Example 1 is generally followed using 10%, 15%, or 20% aqueous sodium hydroxide concentrations. Results appear in Table 1. In each case, the GC yield of ketol A is less than 60%, and the combined selectivities to ketone 1 and ketol A are less than 65%.

TABLE 1

Effect of Base Concentration

| Example | 1 | 2 | 3 | C4 | C5 | C6 |
|---|---|---|---|---|---|---|
| ACA (85%), g | 200 | 200 | 200 | 200 | 200 | 200 |
| MEK, g | 264 | 264 | 264 | 264 | 264 | 264 |
| Water, g | 576 | 594 | 540 | 480 | 420 | 360 |
| 50% NaOH, g | 24 | 6 | 60 | 120 | 180 | 240 |
| NaOH conc., % | 2 | 0.5 | 5 | 10 | 15 | 20 |
| Temp., °C. | 40 | 40 | 40 | 40 | 40 | 40 |
| Time, hours | 8 | 8 | 8 | 8 | 4 | 1 |
| Reaction mixture product composition (%, by GC analysis): | | | | | | |
| ACA | 7.7 | 18 | 13 | 12 | 18 | 25 |
| Ketone 1 | 4.5 | 1.4 | 4.9 | 3.1 | 1.6 | 0.8 |
| Ketone 2 | 0.3 | 0.3 | 0.9 | 1.9 | 2.3 | 2.3 |
| Ketol A | 74 | 69 | 63 | 58 | 51 | 45 |
| Ketol B | 8 | 5.6 | 11 | 18 | 20 | 19 |
| Selectivity (%, by GC analysis): | | | | | | |
| ketone 1 + ketol A | 78 | 71 | 68 | 61 | 52 | 46 |
| All condensation products | 87 | 77 | 80 | 81 | 74 | 68 |

EXAMPLES 7-8 AND COMPARATIVE EXAMPLE 9

Effect of MEK to ACA Molar Ratio

EXAMPLES 7-8

The procedure of Example 1, which uses an MEK to ACA molar ratio of 3, is generally followed, except that the MEK to ACA molar ratio is varied as shown in Table 2. The GC yields of ketol A are consistently greater than 70%. The GC selectivities to ketone 1+ketol A exceed 75%, and selectivity to all condensation products is at least 85% (see Table 2).

COMPARATIVE EXAMPLE 9

The procedure of Example 1 is followed, except that the MEK to ACA molar ratio is reduced to 1:1. The GC yield of ketol A and the GC selectivity to ketone 1+ketol A both dip below 60% (see Table 2).

TABLE 2

Effect of MEK to ACA Molar Ratio

| Example | 1 | 7 | 8 | C9 |
|---|---|---|---|---|
| ACA (85%), g | 200 | 145 | 85 | 200 |
| MEK, g | 264 | 319 | 379 | 88 |
| Water, g | 576 | 576 | 576 | 359 |
| 50% NaOH, g | 24 | 24 | 24 | 15 |
| NaOH conc., % | 2 | 2 | 2 | 2 |
| Mol. ratio MEK:ACA | 3 | 5 | 10 | 1 |
| Temp., °C. | 40 | 40 | 40 | 40 |
| Time, hours | 8 | 8 | 4 | 8 |
| Reaction mixture product composition (%, by GC analysis): | | | | |
| ACA | 7.7 | 7.3 | 7.2 | 31 |
| Ketone 1 | 4.5 | 5.7 | 4.4 | 2.2 |
| Ketone 2 | 0.3 | 0.4 | 0.5 | 0.3 |
| Ketol A | 74 | 72 | 72 | 54 |
| Ketol B | 8 | 9.1 | 8.5 | 5.3 |
| Selectivity (%, by GC analysis): | | | | |
| ketone 1 + ketol A | 78 | 78 | 76 | 56 |
| All condensation products | 87 | 87 | 85 | 62 |

EXAMPLE 10 AND COMPARATIVE EXAMPLES 11-12

Effect of Reaction Temperature

EXAMPLE 10

The procedure of Example 1 is generally followed, except that the reaction temperature is reduced to 25° C. The GC yield of ketol A is 76%. The GC selectivity to ketone 1+ketol A is 78%, and selectivity to all condensation products is 83% (see Table 3).

COMPARATIVE EXAMPLES 11-12

The procedure of Example 1 is generally followed, except that the reaction temperature is increased to 60° C. or 80° C. The GC yields of ketol A fall below (or far below) 50% (see Table 3).

TABLE 3

Effect of Reaction Temperature

| Example | 1 | 10 | C11 | C12 |
|---|---|---|---|---|
| ACA (85%), g | 200 | 200 | 200 | 200 |
| MEK, g | 264 | 264 | 264 | 264 |
| Water, g | 576 | 576 | 576 | 576 |
| 50% NaOH, g | 24 | 24 | 24 | 24 |
| NaOH conc., % | 2 | 2 | 2 | 2 |
| Temp., °C. | 40 | 25 | 60 | 80 |
| Time, hours | 8 | 8 | 8 | 8 |
| Reaction mixture product composition (%, by GC analysis): | | | | |
| ACA | 7.7 | 11 | 11 | 8.6 |
| Ketone 1 | 4.5 | 1.4 | 20 | 43 |
| Ketone 2 | 0.3 | 0.2 | 2.1 | 18 |
| Ketol A | 74 | 76 | 45 | 9.6 |
| Ketol B | 8 | 5.1 | 16 | 14 |
| Selectivity (%, by GC analysis): | | | | |
| ketone 1 + ketol A | 78 | 78 | 65 | 52 |
| All condensation products | 87 | 83 | 83 | 84 |

EXAMPLES 13-16

Effect of Amount of Catalyst Solution

The procedure of Example 1 is generally followed, except that the amount of caustic solution per mole of ACA is varied as shown in Table 4. While ACA conversion is a bit low in Example 13, each of the examples provides, by GC, a product mixture having at least a 65% yield of ketol A, and a combined selectivity of at least 65% of ketone 1 and ketol A.

TABLE 4

Effect of Amount of Catalyst Solution

| Example | 1 | 13 | 14 | 15 | 16 |
|---|---|---|---|---|---|
| ACA (85%), g | 200 | 200 | 200 | 200 | 200 |
| MEK, g | 264 | 264 | 264 | 264 | 264 |
| Water, g | 576 | 222 | 445 | 1336 | 2272 |
| 50% NaOH, g | 24 | 9.3 | 18.6 | 55.7 | 92.8 |
| NaOH conc., % | 2 | 2 | 2 | 2 | 2 |
| Caustic solution (g) per mole of ACA | 536 | 207 | 415 | 1245 | 2115 |
| Temp., °C. | 40 | 40 | 40 | 40 | 40 |
| Time, hours | 8 | 8 | 8 | 4 | 4 |

TABLE 4-continued

Effect of Amount of Catalyst Solution

| Example | 1 | 13 | 14 | 15 | 16 |
|---|---|---|---|---|---|
| Reaction mixture product composition (%, by GC analysis): | | | | | |
| ACA | 7.7 | 19 | 10 | 9.0 | 9.6 |
| Ketone 1 | 4.5 | 1.4 | 3.4 | 5.4 | 9.5 |
| Ketone 2 | 0.3 | 0.1 | 0.4 | 0.5 | 0.7 |
| Ketol A | 74 | 66 | 72 | 72 | 67 |
| Ketol B | 8.0 | 6.8 | 7.7 | 7.7 | 8.6 |
| Selectivity (%, by GC analysis): | | | | | |
| ketone 1 + ketol A | 78 | 68 | 76 | 78 | 76 |
| All condensation products | 87 | 75 | 84 | 86 | 85 |

EXAMPLE 17

Preparation of Ketone 1 from ACA

Part 1 (New catalyst solution): Water (1782 g), aqueous sodium hydroxide (50% aq. NaOH, 72 g), and MEK (793 g) are stirred and heated to 40° C. ACA (668 g of 85% pure material) is added over 30 min. After stirring for 8 h at 40° C., the reaction is deemed complete, and the layers are separated. The catalyst solution (1900 g) is isolated and is reused for Part 2. The organic phase, a solution of ketols in MEK (1340 g), is retained for use in Part 4.

Part 2 (Recycle catalyst solution): The catalyst solution from Part 1 is combined with aqueous sodium hydroxide (3.5 g of 50% aq. NaOH) and MEK (793 g), and the mixture is heated to 40° C. ACA (668 g) is added over 30 min., and the mixture is stirred for 8 h at 40° C. After separating the layers, the catalyst solution (1865 g) is isolated and reused for Part 3. The solution of ketols in MEK (1490 g) is retained for use in Part 4.

Part 3 (Recycle catalyst solution): The catalyst solution from Part 2 is combined with 50% aq. NaOH (3.5 g) and MEK (793 g), and the mixture is heated to 40° C. ACA (668 g) is added as previously described. The isolated catalyst solution (1820 g) can be reused if desired. The solution of ketols in MEK (1504 g) is retained for use in Part 4.

Part 4 (Dehydration): Ketol/MEK solutions from Parts 1-3 (4334 g) are combined, and p-toluenesulfonic acid (9 g) is added. The stirred mixture is heated below 85° C. under vacuum (pressure reduced from 600 mm to 150 mm Hg) to remove MEK and water by distillation. After 5 h, the top phase of the distilled material (1235 g), which is mostly MEK, is collected and is then reused in subsequent experiments.

The distillation pot residue is neutralized with sodium bicarbonate solution (600 g of 3% $NaHCO_3$), and the mixture stirs at 50° C. for 1 h. The layers are separated, and the organic phase (2442 g) is distilled at <2 mm Hg. Fractionation provides a product mixture (1931 g) that contains ketone 1 (89%), ketone 2 (7%), ketone 4 (1%), and ketone 5 (1%). Thus, from 11.2 moles of ACA, 9.2 moles (82%) of ketones 1, 2, 4, and 5 are obtained. The amount of ketone 1 in the distilled product is 1719 g (74% from ACA).

The examples are meant only as illustrations. The following claims define the invention.

We claim:

1. A process which comprises reacting α-campholenic aldehyde (ACA) with methyl ethyl ketone (MEK) in the presence of a base comprising an aqueous alkali metal or alkaline earth metal hydroxide solution under conditions effective to produce a condensation product mixture comprising ketol A and ketone 1 having the structures:

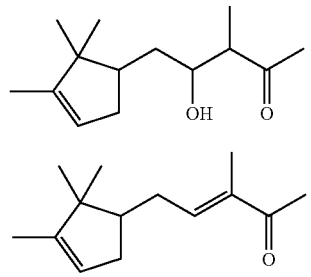

wherein the mixture comprises at least 60 wt. % of ketol A and at least 65 wt. % of ketol A and ketone 1 combined.

2. The process of claim 1 wherein the condensation product mixture comprises at least 70 wt. % of ketol A.

3. The process of claim 1 wherein the condensation product mixture comprises at least 75 wt. % of ketol A and ketone 1 combined.

4. The process of claim 1 wherein the combined yield of all condensation products exceeds 75%.

5. The process of claim 1 wherein the base comprises a solution of 0.5 to 8 wt. % of the aqueous alkali metal or alkaline earth metal hydroxide.

6. The process of claim 1 wherein the base is used in an amount greater than 400 g of solution per mole of ACA.

7. The process of claim 1 wherein the reaction is performed at a temperature within the range of 0° C. to 50° C.

8. The process of claim 1 wherein the molar ratio of MEK to ACA is within the range of 3:1 to 10:1.

9. The process of claim 1 wherein the condensation product mixture is dehydrated in the presence of an organic sulfonic acid to produce a ketone-rich mixture comprising at least 70 wt. % of ketone 1.

10. The process of claim 9 wherein the organic sulfonic acid is p-toluenesulfonic acid.

11. The process of claim 10 comprising less than 1 mole % of p-toluenesulfonic acid based on the amount of ketols in the condensation product mixture.

12. The process of claim 10 wherein water formed in the dehydration step is removed with the aid of an azeotroping solvent, vacuum distillation, or a combination of these.

13. The process of claim 10 wherein the dehydration is performed at a temperature within the range of 25° C. to 120° C.

14. A process which comprises:
(a) reacting ACA with MEK in the presence of a base comprising an alkali metal hydroxide solution under conditions effective to produce a condensation product mixture comprising ketol A and ketone 1 having the structures:

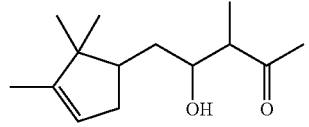

-continued

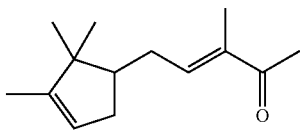

wherein the mixture comprises at least 60 wt. % of ketol A and at least 65 wt. % of ketol A and ketone 1 combined; and (b) dehydrating the condensation product mixture in the presence of p-toluenesulfonic acid to produce a ketone-rich mixture comprising at least 70 wt. % of ketone 1.

15. The process of claim 14 further comprising distilling the ketone-rich mixture to isolate ketone condensation products, wherein the yield of ketone condensation products exceeds 75%.

16. The process of claim 15 wherein the distilled ketone condensation products comprise more than 86 wt. % of ketone 1 or more than 86 wt. % of ketone 1 and ketone 4 combined, where ketone 4 has the structure:

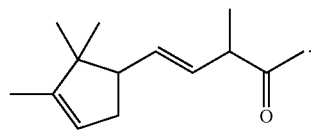

* * * * *